United States Patent [19]
Vancaillie

[11] Patent Number: 5,980,520
[45] Date of Patent: Nov. 9, 1999

[54] DESICCATION ELECTRODE

[76] Inventor: Thierry G. Vancaillie, 27 Headland Road, Castle Cove N.S.W. 2069, Australia

[21] Appl. No.: 09/028,179

[22] Filed: Feb. 23, 1998

Related U.S. Application Data

[63] Continuation-in-part of application No. 08/585,989, Jan. 16, 1996, Pat. No. 5,788,694.

[51] Int. Cl.⁶ .................................................. A61B 17/39
[52] U.S. Cl. ............................................... 606/49; 606/46
[58] Field of Search ........................................ 606/46, 49

[56] References Cited

U.S. PATENT DOCUMENTS

| | | | |
|---|---|---|---|
| 1,680,490 | 8/1928 | Wappler | 128/7 |
| 2,437,329 | 3/1948 | Moore | 128/304 |
| 2,691,370 | 10/1954 | Wallace | 128/6 |
| 2,715,899 | 8/1955 | MacLean | 128/2 |
| 2,936,760 | 5/1960 | Gants | 128/349 |
| 2,990,830 | 7/1961 | Hett | 128/4 |
| 3,636,940 | 1/1972 | Graviee | 128/2 B |
| 3,720,203 | 3/1973 | Brown | 128/4 |
| 4,116,198 | 9/1978 | Roos . | |
| 4,243,049 | 1/1981 | Goodale et al. | 128/757 |
| 4,685,449 | 8/1987 | Bonnet | 128/4 |
| 4,690,175 | 9/1987 | Ouchi et al. | 138/131 |
| 4,693,704 | 9/1987 | Ogita | 604/55 |
| 4,765,314 | 8/1988 | Kolditz et al. | 128/4 |
| 4,779,611 | 10/1988 | Grooter et al. | 128/4 |
| 4,813,429 | 3/1989 | Eshel et al. | 128/736 |
| 4,836,187 | 6/1989 | Iwakoshi et al. | 128/4 |
| 4,841,952 | 6/1989 | Sato et al. | 128/6 |
| 4,860,731 | 8/1989 | Matsura | 128/6 |
| 4,889,106 | 12/1989 | Wantanabe | 128/4 |
| 4,979,498 | 12/1990 | Oneda et al. | 128/6 |
| 4,998,527 | 3/1991 | Meyer | 128/6 |
| 5,025,778 | 6/1991 | Silverstein et al. | 128/4 |
| 5,030,227 | 7/1991 | Rosenbluth et al. | 604/9 |
| 5,031,603 | 7/1991 | Gautier et al. | 128/4 |
| 5,127,393 | 7/1992 | McFarlin et al. | 128/4 |
| 5,147,353 | 9/1992 | Everett | 606/15 |
| 5,152,277 | 10/1992 | Honda et al. | 128/4 |
| 5,156,590 | 10/1992 | Vilmar | 604/4 |
| 5,188,596 | 2/1993 | Condon et al. | 606/101 |
| 5,196,011 | 3/1993 | Korth et al. . | |
| 5,213,093 | 5/1993 | Swindle | 128/4 |
| 5,230,621 | 7/1993 | Jacoby | 433/29 |
| 5,285,795 | 2/1994 | Ryan et al. | 128/750 |
| 5,303,719 | 4/1994 | Wilk et al. | 128/898 |
| 5,314,443 | 5/1994 | Rudnick | 606/192 |
| 5,325,845 | 7/1994 | Adair | 128/4 |
| 5,328,365 | 7/1994 | Jacoby | 433/29 |
| 5,582,610 | 12/1996 | Grossi et al. | 606/46 |
| 5,669,906 | 9/1997 | Grossi et al. | 606/46 |
| 5,779,700 | 7/1998 | Hahnen et al. | 606/46 |
| 5,782,829 | 7/1998 | Swiatek et al. | 606/49 |

FOREIGN PATENT DOCUMENTS

| | | |
|---|---|---|
| 0419235 | 3/1991 | European Pat. Off. . |
| 1548389 | 10/1968 | France . |

OTHER PUBLICATIONS

C.J.G. Sutton, et al., "Endometrial Resection", *Endometrial Ablation*, Churchill Livingstone, 1993, pp. 91–131.

*Primary Examiner*—Lee Cohen
*Attorney, Agent, or Firm*—Fish & Richardson P.C.

[57] ABSTRACT

A tissue desiccating electrode has first and second longitudinal members each with proximal and distal ends. A tip member couples the longitudinal members proximate the distal ends thereof and has a centrally-positioned, transversely-extending, fixed protuberance. The protuberance has an outer perimeter with an overall smoothly curved base and a plurality of cooling grooves. The grooves penetrate inwardly from the outer perimeter.

20 Claims, 2 Drawing Sheets

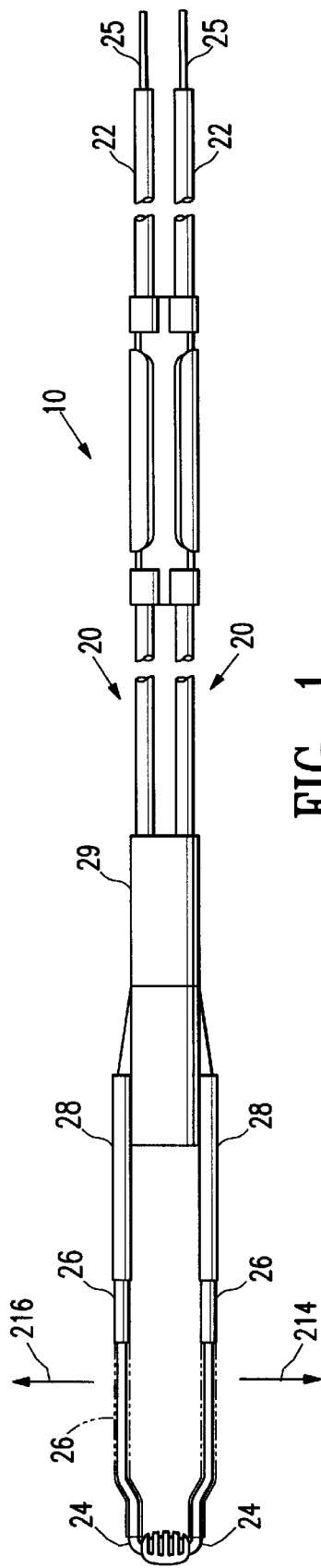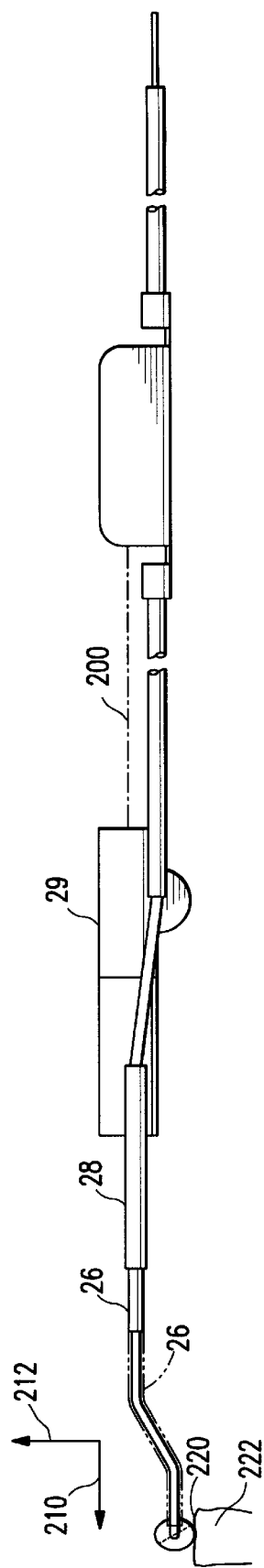

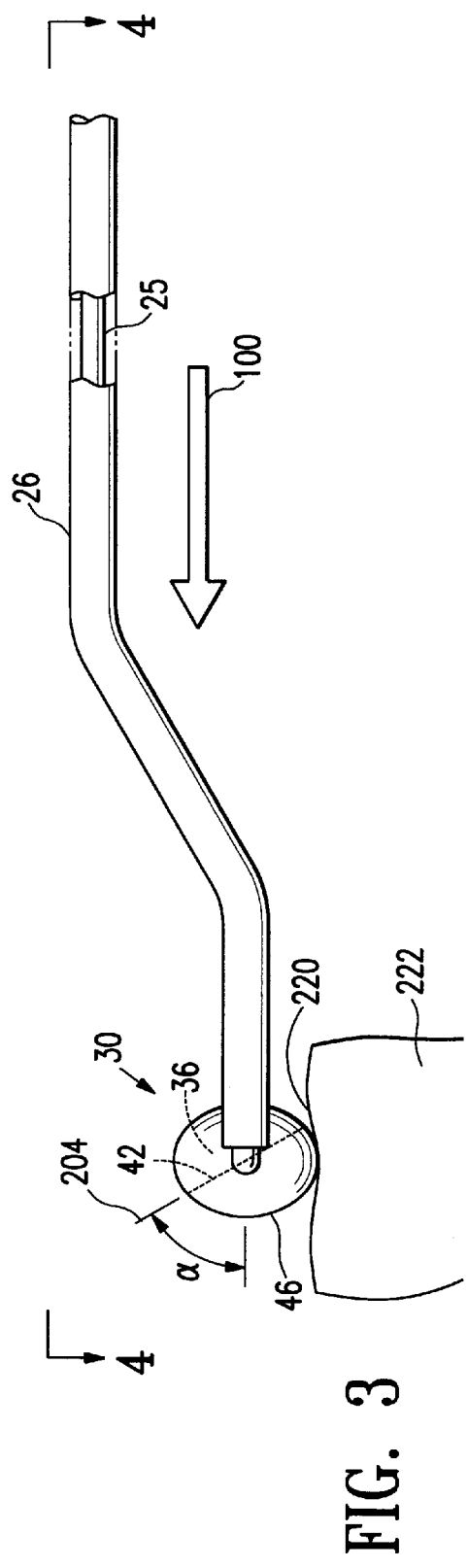
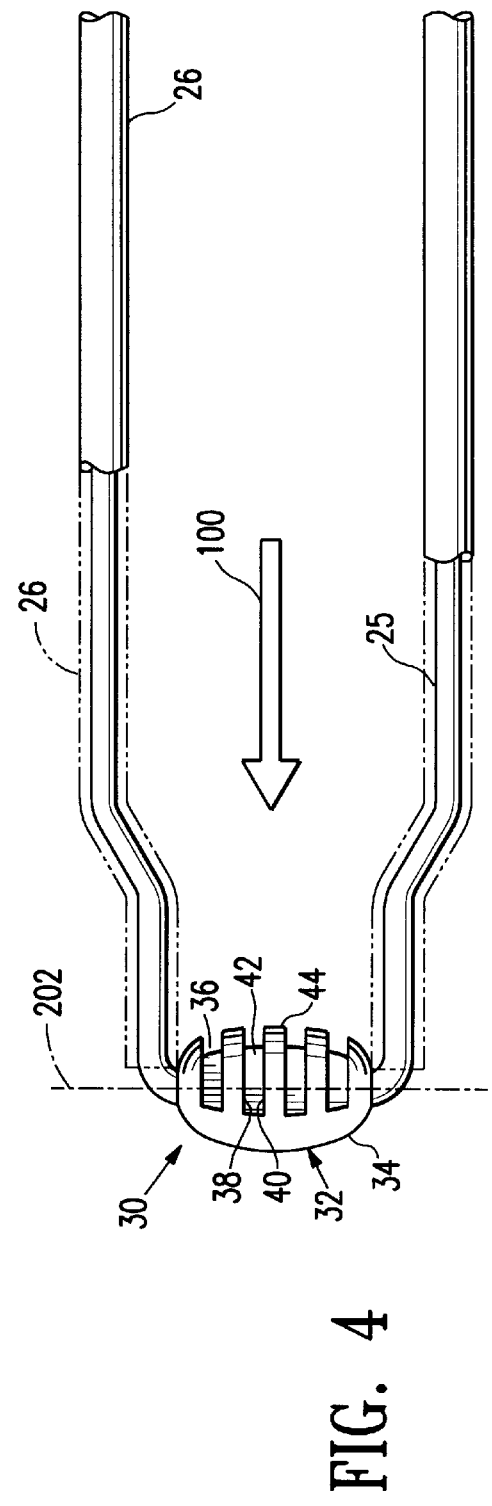
FIG. 3
FIG. 4

DESICCATION ELECTRODE

RELATED UNITED STATES PATENT APPLICATIONS

This application is a continuation-in-part of U.S. patent application Ser. No. 08/585,989 filed on Jan. 16, 1996, now U.S. Pat. No. 5,788,694.

BACKGROUND

1. Technical Field

This invention relates to surgery, and more particularly to electrodes for surgical resectoscopes.

2. Background Information

A variety of resectoscopes have been developed and are known for purposes of tissue resection. Common applications are in cystoscopy and, more recently, in hysteroscopy. The use of resectoscopes in a variety of other applications is an evolving area.

A main component of a resectoscope is commonly referred to as "the working element". The working element comprises an electrode mounted into a reciprocating mechanism that can be moved forward and backward between retracted and extended positions. The electrode includes a distal tip and one or more conductors extending longitudinally back through the sheath. In the retracted position the electrode tip resides within an outer sleeve or tube which protects the tip from interaction with the patient's body and vice versa. In the extended position, the electrode tip extends forward of the end of the protective sleeve for engaging the patient's tissue. The mechanism may either be passive or spring loaded. In the latter case, a typical configuration involves the spring biasing the electrode into the retracted position.

For visualization of the interaction of the electrode with the patient's tissue, an optical element is typically inserted within the sheath. The optical element, often referred to as the "telescope" has a typical diameter of approximately 4 mm. Depending on the application and the preferences of the surgeon, the telescope may be provided with a variety of depths and angles of view. For prostate resection and other urologic applications, angles of up to 120° are often preferred. In uterine applications, preferred angles of view may vary between 0° and 30°. A depth of field is typically infinite, with a focal length of approximately 2 cm. Such a focal length may cause size distortions but provides the skilled surgeon with necessary information to guide the electrode.

The resectoscope electrode tip is an "active" electrode. In a typical system, a complete circuit is formed with a plate-like "dispersive" or grounding electrode often placed in contact with a relatively wide area of the patient's back. The grounding electrode is coupled to the active electrode via a voltage generator for creating a potential between these two electrodes. A wide variety of voltages, frequencies, patterns, etc. may be involved depending upon the application and the choices of the equipment designer and surgeon. Tissue cutting or removal may then be accomplished by arcing between the active electrode and the patient's tissue or by resistive heating of the patient's tissue in contact with the active electrode.

Broadly defined, two major classes of electrodes are cutting electrodes and desiccation electrodes. In the latter, the electrode tip interacts with a tissue surface within the patient. In the former, the electrode is typically formed as a wire loop which is typically used to make a penetrating cut. The loop may be plunged beneath the tissue surface and then moved parallel to the surface to remove a layer of tissue.

Desiccation electrodes (typically including electrodes designated as "coagulation" electrodes) are drawn over the surface of the tissue in order to desiccate the tissue by resistive heating of the tissue in contact with the electrode tip. Such electrodes generally involve creating a large contact area with the tissue. Many such electrodes feature a spherical electrode surface in contact with the tissue surface. A common configuration of this type of electrode involves a hemispherical shell with its convex surface facing down (toward and in contact with the tissue surface). Another common type is the "roller" electrode which is frequently formed as a right circular cylinder extending transverse to the resectoscope axis and free to pivot about its own central axis. Such an electrode is rolled over the tissue surface by the reciprocation of the working element. The rolling action of the roller-type electrode helps to maintain consistent temperature. However, rolling electrodes often suffer from inadequate electrical contact between the conductor(s) and the rolling element as the contact areas between the two may become corroded or contaminated. Additionally, cylindrical electrodes often suffer from an "edge effect" wherein the current density between the patient and the electrode is concentrated toward the ends of the roller rather than having a more even distribution.

Use of a resectoscope creates a variety of byproducts, including cut and coagulated tissue which must be removed in order to maintain the ease and effectiveness of the procedure. It is also desired to distend the patient's tissues to facilitate the tissue removal procedure. These goals may be accomplished via the introduction of a fluid into the patient. Early use of the resectoscope involved cystoscopy of the bladder. In such a case, the bladder could be filled with a fluid and the procedure performed. At various intervals, the bladder could be drained and refilled. In other applications such as hysteroscopy, there are not the same fluid retention capabilities as exist with the bladder. Accordingly, the continuous flow resectoscope was introduced. A typical continuous flow resectoscope includes an outer tubular sheath and an inner tube concentric therewith. An annular space between the sheath and tube provides an outflow conduit, and an annular space between the tube and telescope provides an inflow conduit for introducing clean fluid to the patient. Such devices are generally described in U.S. Pat. Nos. 3,835,842 and 4,134,406 of Jose J. Iglesias, the disclosures of which are incorporated herein by reference.

SUMMARY OF THE INVENTION

According to one aspect, the invention is directed to a tissue desiccating electrode having first and second longitudinal members each with proximal and distal ends. A tip member couples the longitudinal members proximate the distal ends thereof and has a centrally-positioned, transversely-extending, fixed protuberance. The protuberance has an outer perimeter with an overall smoothly curved base and a plurality of cooling grooves. The grooves penetrate inwardly from the outer perimeter.

Implementations of the invention may include one or more of the following. The protuberance may be transversely elongate. The protuberance may be generally ellipsoidally shaped. The protuberance may be doubly convex. The protuberance may be solid. The cooling grooves may be longitudinally-extending. The cooling grooves may be vertically-extending. The cooling grooves may face in a direction intermediate a rearward direction and an upward direction. The cooling grooves may generally face in a direction approximately 60° from the upward direction. At least one of the longitudinal members may be a conductor.

The cooling grooves may each have a generally planar bottom. The cooling grooves may each have a pair of generally vertically extending sides. There may preferably be between three and six cooling grooves.

According to another aspect, the invention is directed to a tissue desiccating electrode having first and second longitudinal members each with proximal and distal ends. A tip member is coupled to the longitudinal members proximate the distal ends thereof. The tip member has a centrally-positioned, transversely-extending, fixed protuberance. The protuberance has an outer perimeter with a base portion for engaging the tissue and has a plurality of cooling elements. The cooling elements face generally away from the base and have surfaces not in contact with the tissue. The cooling elements may be lands formed between channels penetrating inwardly from an external perimeter surface of the protuberance.

In another aspect, the invention is directed to a method of making a tissue desiccation tip. The tip comprises cooling means and the method includes coupling a solid structure of a relatively larger cross-sectional area to an electrical conductor. The method further includes deforming the solid structure to increase surface area so as to make a tissue desiccation tip comprising cooling means.

The invention facilitates a cooling of the desiccation electrode used in a continuous flow resectoscope. The invention provides for increased tip surface area in contact with fluid flow from the resectoscope. This enhances heat transfer from the tip to the fluid. With the protuberance fixed, electrical contact between the conductor and the protuberance is constant rather than through a sliding of surfaces in a rolling electrode.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a top view of a desiccation electrode according to the present invention.

FIG. 2 is a side view of the electrode of FIG. 1.

FIG. 3 is a side view of the tip of the electrode of FIG. 1.

FIG. 4 is a top view of the tip of the electrode of FIG. 1.

Like reference numbers and designations in the various drawings indicate like elements.

DETAILED DESCRIPTION

FIGS. 1 and 2 show an electrode 10 having at least one longitudinal electrical conductor 20 (two being shown for the preferred embodiment). The electrode is preferably configured for use with an appropriate continuous flow resectoscope (not shown). The electrode 10 has a central longitudinal axis 200 which is parallel and substantially coincident with the longitudinal axis of the resectoscope with which the electrode is used.

Each conductor 20 has a proximal end 22 and a distal end 24. Each conductor may include an electrically conductive core 25 and one or more generally concentric layers of electrical insulation 26 in various combinations along the length of the conductor 20. A variety of layering arrangements of conductive and insulative layers are possible. Concentric outer metal tubes 28 may be fitted over insulation 26 for added stiffness and strength and may be rigidly coupled (such as by welding, soldering or unitarily forming) to a telescope guide tube 29 which receives as the optical element (not shown).

A desiccating electrode tip 30 is coupled to the conductors 20 proximate the distal ends 24 of the conductors. The tip 30 is electrically coupled to at least one conductive core 25 or other conductive layers so that a voltage may be applied to the tip.

For purposes of exposition, the electrode axis 200 which is coincident with the direction of reciprocation of the working element defines a forward direction 210, a rearward direction being opposite thereto. An upward direction 212 is generally defined orthogonal to the forward direction 210 and pointing away from the surface 220 of the tissue 222 being desiccated. Left and right directions 214 and 216 correspond to the left and right sides of a surgeon using the resectoscope when the resectoscope's upward direction 212 corresponds to the true upward direction.

As shown in FIGS. 3 and 4, the tip 30 is formed having a centrally-positioned, transversely-extending, fixed protuberance 32.

The overall outer perimeter surface of the protuberance 32 is generally doubly curved and approximately defined as ellipsoidal although it may not be represented by a true mathematical ellipsoid. Capsule-shaped or round surfaces may also be possible. The protuberance has a central axis 202 which is transverse to the electrode axis 200 and to the direction of reciprocation. The perimeter surface is doubly curved and generally symmetric about the axis 202. In the exemplary embodiment, the protuberance 32 has a central diameter of approximately 0.14 inches and a width of approximately 0.24 inches.

The exterior surface 34 of the protuberance includes an intact portion of the ellipsoidal overall outer perimeter surface and is further defined by a plurality of open grooves or channels 36 each having substantially flat left and right sides 38 and 40 and a substantially flat bottom 42 connecting the left and right sides. The channels are open to the ellipsoidal overall outer perimeter surface portion and connect therewith to form the exterior surface 34 of the protuberance. In the illustrated embodiment, the channel sides or walls 38 and 40 are all vertically and longitudinally-extending. The channel bottoms or bases 42 are coplanar with each other in a transversely-extending plane 204 at an angle α to the resectoscope axis 200. In the illustrated embodiment, there are four channels each extending about half way through the protuberance, so that the plane 204 includes the axis 202. The width of the grooves or channels 36 is approximately equal to that of the coding or fins lands 44 formed between the channels. The lands are defined by the sides of adjacent channels and the intact portion of the ellipsoidal perimeter surface between those channels. An exemplary groove/land width is 0.025 inches.

On the opposite side of the plane 204 from the grooves 36 is a smoothly curved base section 46 which is a subportion of the intact elliposal perimeter surface. During operation of the resectoscope, the base 46 (FIG. 3) engages the tissue surface 220 and resistively heats the tissue surface 220 to desiccate the tissue. A remaining portion of the protuberance 32 including the grooves 36 and their associated lands 44 does not engage the tissue, but rather is open and exposed to a flow of liquid 100 (which may serve distention, visualization, and cooling purposes). Such liquid may be provided in a conventional manner by the continuous flow resectoscope.

The increased surface area of the protuberance provided by the channels 36 and their associated lands 44 serves as a heat sink to cool the protuberance when the channel sides and bottom are exposed to the flow of cooling liquid introduced by the resectoscope. Preferably, the heat sink properties are sufficient to maintain the protuberance at a temperature of about 80° C or less so as to avoid carbonization of the tissue and cavitization of the liquid.

As shown in FIG. 3, to keep the base in contact with the tissue surface and the grooves exposed to the flow of liquid, the grooves generally face upward. In particular, the grooves generally face in the direction intermediate the rearward and upward directions. Most particularly, the angle α is approximately 60° so that the grooves generally face a direction approximately 60° from the upward direction.

In the illustrated embodiment, the protuberance is preferably solid and formed of a highly thermally conductive material such as stainless steel.

In the illustrated embodiment, the overall perimeter surface of the protuberance is ellipsoidal. Configurations in which the protuberance is asymmetric about the transverse axis 202 are also possible. The illustrated geometry results in part from its ease of manufacture wherein the protuberance may be easily machined and the grooves then cut into the protuberance. Other configurations may be formed such as configurations in which the protuberance is cast or molded and the grooves are formed between fins projecting away from the protuberance.

A number of embodiments of the present invention have been described. Nevertheless, it will be understood that various modifications may be made without departing from the spirit and scope of the invention. For example, the electrode may be manufactured for use with a variety of resectoscopes. The particular resectoscope with which the electrode is to be used will influence a variety of construction details. A variety of electrode orientations and groove/land configurations are also possible as are a variety of materials. Accordingly, other embodiments are within the scope of the following claims.

What is claimed is:

1. A tissue desiccating electrode comprising:

a first longitudinal member, having a proximal end and a distal end;

a second longitudinal member, having a proximal end and a distal end, wherein at least one of the first longitudinal member and second longitudinal member is a conductor; and a tip member coupled to the first longitudinal member proximate the distal end thereof and coupled to the second longitudinal member proximate the distal end thereof, the tip member having a centrally positioned, transversely extending thermally conductive fixed protuberance, having an outer perimeter with an overall smoothly curved base and a plurality of cooling grooves, penetrating inwardly from the outer perimeter.

2. The electrode of claim 1, wherein the protuberance is transversely elongate.

3. The electrode of claim 1, wherein the protuberance is generally ellipsoidally shaped.

4. The electrode of claim 3, wherein the cooling grooves generally face a direction intermediate a rearward and an upward direction.

5. The electrode of claim 4, wherein the cooling grooves generally face a direction approximately sixty degrees from the upward direction.

6. The electrode of claim 1, wherein the protuberance is doubly convex.

7. The electrode of claim 1, wherein the protuberance is solid.

8. The electrode of claim 1, wherein the cooling grooves are longitudinally extending.

9. The electrode of claim 1, wherein the cooling grooves are vertically extending.

10. The electrode of claim 1, wherein at least one of the first longitudinal member and second longitudinal member has a conductive core.

11. The electrode of claim 1, wherein the cooling grooves each have a generally planar bottom.

12. The electrode of claim 1, wherein the cooling grooves each have a pair of generally vertical extending sides.

13. The electrode of claim 1, wherein there are between three and six said cooling grooves.

14. A tissue desiccating electrode comprising:

a first longitudinal member, having a proximal end and a distal end;

a second longitudinal member, having a proximal end and a distal end, wherein at least one of the first longitudinal member and second longitudinal member is a conductor; and a tip member coupled to the first longitudinal member proximate the distal end thereof and coupled to the second longitudinal member proximate the distal end thereof, the tip member having a centrally positioned, transversely extending thermally conductive fixed protuberance, having an outer perimeter with a base portion for engaging the tissue and a plurality of cooling elements, facing generally away from the base portion, the cooling elements having surfaces adapted not to be in contact with the tissue.

15. The electrode of claim 14, wherein the cooling elements are lands formed between channels penetrating inwardly from an external perimeter surface of the protuberance.

16. A tissue desiccating electrode comprising:

at least one longitudinally-extending conductor, having a proximal end and a distal end;

a tip member coupled to the conductor proximate the distal end thereof and having a centrally positioned thermally conductive fixed protuberance, the protuberance having an outer perimeter with a base portion for engaging the tissue and a plurality of cooling fins facing generally away from the base portion, the cooling fins having surfaces adapted not to be in contact with the tissue.

17. The electrode of claim 16, wherein the base portion is doubly curved.

18. The electrode of claim 17, wherein the cooling elements are lands formed between channels penetrating inwardly from an external perimeter surface of the protuberance.

19. A tissue desiccating electrode comprising:

a first longitudinal member, having a proximal end and a distal end;

a second longitudinal member, having a proximal end and a distal end, wherein at least one of the first longitudinal member and second longitudinal member is a conductor; and a tip member coupled to the first longitudinal member proximate the distal end thereof and coupled to the second longitudinal member proximate the distal end thereof, the tip member having a centrally positioned, transversely extending thermally conductive fixed protuberance, having an ellipsoidal shape with an overall smoothly curved base and a plurality of cooling grooves, facing a direction intermediate a rearward and an upward direction.

20. The electrode of claim 19, wherein the cooling grooves generally face a direction approximately sixty degrees from the upward direction.

* * * * *